United States Patent
Chen

(10) Patent No.: US 10,478,419 B2
(45) Date of Patent: Nov. 19, 2019

(54) USE OF DAPHNORETIN IN PREVENTION OF TISSUE OR ORGAN TRANSPLANT REJECTION OR GRAFT-VERSUS-HOST-DISEASE

(71) Applicant: MacKay Memorial Hospital, Taipei (TW)

(72) Inventor: Yu-Jen Chen, Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 0 days.

(21) Appl. No.: 16/038,198

(22) Filed: Jul. 18, 2018

(65) Prior Publication Data

US 2019/0022057 A1 Jan. 24, 2019

Related U.S. Application Data

(60) Provisional application No. 62/535,247, filed on Jul. 21, 2017.

(51) Int. Cl.
*A61K 31/366* (2006.01)
*A61P 37/06* (2006.01)
*A61K 31/436* (2006.01)
*A61K 45/06* (2006.01)
*A61K 31/137* (2006.01)

(52) U.S. Cl.
CPC ........... *A61K 31/366* (2013.01); *A61K 31/137* (2013.01); *A61K 31/436* (2013.01); *A61K 45/06* (2013.01); *A61P 37/06* (2018.01)

(58) Field of Classification Search
CPC .................................................. A61K 31/366
See application file for complete search history.

(56) References Cited

PUBLICATIONS

Chen et al. "Daphnoretin modulates differentiation and maturation of human dendritic cells through down-regulation of c-Jun N-terminal kinase", International Immunopharmacology 51 (2017) 25-30, Elsevier, Aug. 1, 2017.

*Primary Examiner* — Svetlana M Ivanova

(57) ABSTRACT

Disclosed herein are methods of using daphnoretin to treat, prevent or reduce the incidence of organ transplant rejection and graft-versus-host disease (GVHD). According to embodiments of the present disclosure, daphnoretin is administered to the recipient subject or to the donor organ prior to the transplantation to reduce immune response in the recipient subject against the transplanted organ, or to lower the risk of developing GVHD in the recipient subject.

11 Claims, 8 Drawing Sheets
(2 of 8 Drawing Sheet(s) Filed in Color)

A.

B.

C.

D.

E.

A.

B.

C.

A.

B.

USE OF DAPHNORETIN IN PREVENTION OF TISSUE OR ORGAN TRANSPLANT REJECTION OR GRAFT-VERSUS-HOST-DISEASE

CROSS-REFERENCE TO RELATED APPLICATIONS

This application claims priority of U.S. provisional patent application Ser. No. 62/535,247, filed Jul. 21, 2017. The content of which is incorporated herein in its entirety by reference.

STATEMENT REGARDING PRIOR DISCLOSURES BY THE INVENTOR OR A JOINT INVENTOR UNDER 37 C.F.R. 1.77(B)(6)

Part of the subject matter of the invention described in the present application was published by the inventor, Yu-Jen CHEN in an article titled "Daphnoretin modulates differentiation and maturation of human dendritic cells through down-regulation of c-Jun N-terminal kinase." The article was published on Aug. 1, 2017 in *International Immunopharmacology* 51, 25-30. The publication was made by and/or originated from the inventive entity of the present invention, and the entirety of this article is incorporated herein by reference. A copy of the article is provided in a concurrently filed Information Disclosure Statement pursuant to the guidance of 78 Fed. Reg. 11076 (Feb. 14, 2013)."

BACKGROUND OF THE INVENTION

1. Field of the Invention

The present disclosure in general relates to the field of transplant rejection; more particularly to the use of daphnoretin in the treatment or prophylaxis of tissue or organ rejection or graft-versus-host-disease (GVHD).

2. Description of Related Art

Daphnoretin (7-hydroxy-6-methoxy-3,7'-dicoumaryl ether) is a naturally occurring bicoumarin compound isolated from *Wikstroemia indica* C.A. It has been reported to possess bioactivity in suppressing the expression of hepatitis B surface antigen and inactivating protein kinase C (PKC) with translocation of PKC from the cytosol to the membrane and down-regulating intracellular PKC level in human hepatoma Hep3B cells. Daphnoretin has also been reported to possess anti-cancer activity against Ehrlich ascites tumor, cervical cancer and lung adenocarcinoma. However, the effect of daphnoretin on the differentiation and maturation of dendritic cells (DCs) has never been reported.

Inventors of the present disclosure unexpected discovered that daphnoretin may suppress the differentiation of dendritic cells, thus is useful as a lead compound for the development of a medicament for the treatment and/or prophylaxis of tissue or organ rejection or graft-versus-host disease (GVHD).

SUMMARY

The present disclosure aims at providing a method for treating a tissue or organ transplant rejection or GVHD in a subject. The method comprises administering to the subject an effective amount of daphnoretin to attenuate the tissue or organ transplant rejection.

According to some embodiments of the present disclosure, the daphnoretin is administered to the subject prior to transplantation.

According to further embodiments of the present disclosure, the present method further comprises the step of, administering the daphnoretin to the donor tissue or organ prior to transplantation.

According to embodiments of the present disclosure, the tissue may be a skin, a stem cell, or bone marrow.

According to embodiments of the present disclosure, the organ may be kidney, heart, liver, lung, or pancreas.

According to preferred embodiments of the present disclosure, the daphnoretin is administered to the subject in the range of 0.1-100 mg/Kg. Preferably, the daphnoretin is administered in the range of 1-50 mg/Kg.

According to some embodiments of the present disclosure, the daphnoretin may be administered parenterally, such as, subcutaneously, intramuscularly, intraperitoneally, intravenously, intraarterially, intramyocardially, or intrathecally.

According to other embodiments of the present disclosure, the daphnoretin may be administered orally, such as, buccal, and enteral or intragastric administration.

Accordingly to optional embodiments of the present disclosure, the method may further include the step of administering to the subject an immunosuppressive agent, prior to, concurrently with, or after the administration of daphnoretin.

According to preferred embodiments of the present disclosure, the immunosuppressive agent may be selected from the group consisting of cyclosporine, dexamethasone, prednisone, azathioprine, fluorouracil, mercaptopurine, everolimus, sirolimus, tacrolimus, methotrexate, anthracycline, bleomycin, dactinomycin, mithramycin, mitomycin, rapamycin, and mycophenolate mofetil.

According to one preferred embodiment of the present disclosure, the immunosuppressive agent is rapamycin.

According to preferred embodiments of the present disclosure, the subject is a human.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of the specification, illustrate various example systems, methods and other exemplified embodiments of various aspects of the invention. The present description will be better understood from the following detailed description read in light of the accompanying drawings, where, FIG. 1 are photographs illustrating the effect of daphnoretin on the morphology of monocyte-derived DCs in accordance with one embodiment of the present disclosure, magnification of photograph is 400×, where A. the control DCs, B. 1.1 µM daphnoretin, C. 3.3 µM daphnoretin, D. 10 µM daphnoretin, and E. 30 µM daphnoretin.

DETAILED DESCRIPTION OF THE INVENTION

Figure 1:
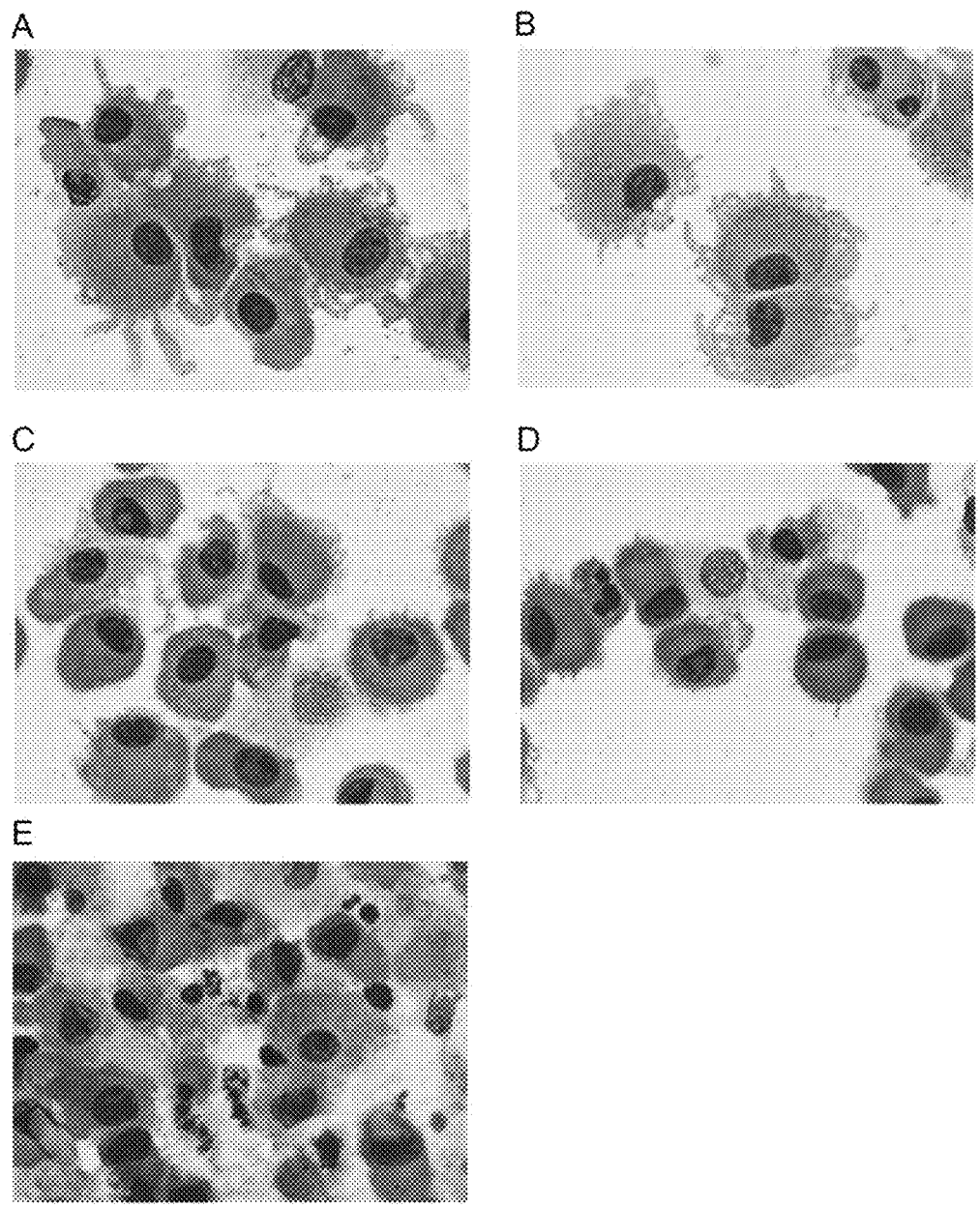

The detailed description provided below in connection with the appended drawings is intended as a description of the present disclosure and is not intended to represent the only forms in which the present disclosure may be constructed or utilized.

1. Definitions

The term "donor" as used herein refers to the subject that provides the organ and/or tissue transplant or graft to be transplanted to the recipient or host.

The terms "recipient" and "host" are interchangeably used in the present test, and refers to the subject that receives a tissue and/or organ transplant or graft.

The term "graft" as used herein refers to the tissue and/or organ that is transplanted or implanted into the host or recipient.

The term "tissue" as used herein refers to a group or collection of similar cells and the intercellular substances which act together to perform a particular function. Primary tissues include epithelial, connective, muscular and nervous tissues.

The term "organ" as used herein refers to a group of several tissue types that perform a given function. Exemplary organs include, but are not limited to, heart, kidney, liver, pancreas, and lung.

The term "tissue or organ transplant rejection" as used herein refers to a consequence of tissue or organ transplantation caused by the recipient's or host's immune system in response to the transplanted tissue/organ, which can damage or destroy the transplanted tissue/organ. Thus, one of skilled artisan in the art is fully aware that "tissue or organ transplant rejection" is controlled by the host subject.

The term "graft-vs-host-disease" or "GVHD" as used herein is the pathological reaction that occurs between the host and the grafted tissue. The grafted or donor tissue dominates the pathological condition. GVHD can be seen following stem cell and/or solid tissue or organ transplantation. GVHD occurs in immunocompromised subjects, who when transplanted, receive "passenger" lymphocytes in the transplanted stem cells and/or solid tissue or organ. These lymphocytes recognize the recipient's tissue or organ as foreign. Thus, they attack and mount an inflammatory and destructive response in the recipient. GVHD has a predilection for epithelial tissues, such as skin, liver, and mucosa of the gastrointestinal tract. GVHD subjects are immunocompromised due to the fact that prior to transplant of the graft, the subject receives immunosuppressive therapy.

Unless otherwise indicated, the term "effective amount" as referred to herein designate the quantity of a compound which is sufficient to yield a desired response, such as improvement or remediation of transplant rejection. For therapeutic purposes, the effective amount is also one in which any detrimental effects of the compound are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the daphnoretin of the present disclosure), such as molar concentration, mass concentration, volume concentration, molality, mole fraction, mass fraction and mixing ratio. Further, persons having ordinary skills in the related art could calculate the human equivalent dose (HED) for the medicament (such as the compound of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

Unless otherwise indicated, the terms "treat," "treating" and "treatment" contemplate the action of administering to a patient an effective amount of daphnoretin so that the patient suffering from tissue and/or organ rejection, exhibits an improvement related to allograft tissue and/or organ acceptance. The improvement is any observable or measureable improvement, thus, a skilled artisan would understand that a treatment may improve the patient condition, but may not be a complete cure of the disease.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Treatment of Tissue and/or Organ Transplant Rejection by Daphnoretin

Inventors of the present disclosure unexpectedly identify that daphnoretin, a compound obtained through isolation and purification from natural sources, such as, *Wikstroemia indica* C.A. may suppress the differentiation and maturation of human myeloid dendritic cells (DCs), thus is useful as a lead compound for the development of a medicament for the treatment and/or prophylaxis of tissue or organ rejection.

In general, the daphnoretin may be isolated in accordance with procedures described previously (Ko et al., (1993) Biochem J. 295, 321-327.). Alternatively, it may also be obtained from any commercial sources.

In accordance with the present disclosure, methods for treating a tissue or organ transplant rejection or graft-versus-host disease (GVHD) in a subject are provided. To this purpose, an effective amount of daphnoretin is administered as a therapeutic drug to a subject who has undergone tissue and/or organ transplant (e.g., skin, kidney, lung, liver, heart, bone marrow, peripheral stem cells and etc), and/or a prophylactic drug to tissue and/or organ transplant, for example, bone marrow (BM) or peripheral stem cell donor cells, to prevent the development of GVHD in recipients and/or to prevent or attenuate transplant rejection in the recipients.

According to some embodiments of the present disclosure, the purpose of treating, preventing or reducing the risk of developing GVHD in a subject is achieved by administering to the donor organ or donor tissue an effective amount of daphnoretin prior to transplantation. It is envision that administering daphnoretin to the donor tissue and/or organ will attenuate the immune cells in the donor tissue/organ and prevent the development of the immune response that is mounted against the recipient's tissue, thus preventing or attenuating GVHD.

According to additional embodiments of the present disclosure, a method of treating, preventing or attenuating the severity of tissue or organ transplant rejection in a recipient is provided. The method includes the step of administering an effective amount of daphnoretin to the donor in an amount sufficient to attenuate the tissue or organ transplant rejection in the recipient. It is envision that administering daphnoretin could reduce allogeneic immune response in the recipient.

According to some embodiments of the present disclosure, a tissue graft (e.g., skin) is transplanted, which may be part or separated from an organism. In additional embodiments, an organ is used as the graft.

One of skill in the art can determine the subject, whom would potentially benefit from a therapeutic agent that would reduce chronic allograft rejection and toxicity associated with standard therapy, or the development of GVHD. One of skill in the art can also determine the effective amount of daphnoretin to be administered to a subject based on several parameters, such as local effects, pharmacodynamics, absorption, metabolism, method of delivery, age, weight, disease severity, and response to the therapy.

According to preferred embodiments of the present disclosure, the daphnoretin is administered to the subject in the range of 0.1-100 mg/Kg, such as 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 mg/Kg; preferably, in the amount of about 1-50 mg/Kg, such as 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 mg/Kg.

According to certain embodiments of the present disclosure, the daphnoretin may be given in a single dose or multiple doses. The single dose may be administered daily, or multiple times a day, or multiple times a week, or monthly, or multiple times a month. In other embodiments, the daphnoretin is given in a series of doses. The series of doses may be administered daily, or multiple times a day, weekly, or multiple times a week, or monthly, or multiple times a month.

According to some embodiments, the daphnoretin may be administered orally, such as buccal, and enteral or intragastric administration. It is also envisioned that daphnoretin may be used as a food additive. For example, it may be sprinkled on food or added to a liquid prior to ingestion. Additionally or optionally, the daphnoretin may be administered in conjunction with an antiacid. Thus, the antiacid is administered prior to, or concurrently with, or after the administeration of daphnoretin. The administeration of the antiacid prior to, or simultaneously with daphnoretin may help reduce the degree of inactivation of daphnoretin in the digestive tract. Any known antiacids may be used, such as sodium bicarbonate, magnesium oxide, magnesium hydroxide, calcium carbonate, magnesium carbonate, and aluminium hydroxide gel and etc.

According to preferred embodiments of the present disclosure, the daphnoretin may be administered parenterally, such as, subcutaneously, intramuscularly, intraperitoneally, intravenously, intraarterially, intramyocardially, or intrathecally.

The improvement resulted from the present method is any observable or measurable improvement. Thus, one of skill in the art may realize that a treatment may improve the subject's condition, but may not be a completer cure of the disease. In certain aspects, the daphnoretin is administered in an effective amount to decrease, reduce, inhibit or suppress the level of an immune response against a graft in the recipient. In further aspects, an improvement may consist of any of the following, for example, increased survival of a skin graft, increased urine output of a kidney graft, decreased jaundice for a liver graft, or increased in overall tolerance of the graft in the recipient. Thus, after administration of daphnoretin, any of the above conditions is improved, then the amount of daphnoretin is considered to be an effective amount.

3 Combinational Use and Kits

Additionally or optionally, any methods described above may further include the step of administering an immunosuppressive agent, prior to, concurrently with, or after the administration of daphnoretin.

According to preferred embodiments of the present disclosure, the immunosuppressive agent may be selected from the group consisting of cyclosporine, dexamethasone, prednisone, azathioprine, fluorouracil, mercaptopurine, everolimus, sirolimus, tacrolimus, methotrexate, anthracycline, bleomycin, dactinomycin, mithramycin, mitomycin, rapamycin, and mycophenolate mofetil. According to one preferred embodiment of the present disclosure, the immunosuppressive agent is rapamycin.

Also encompasses within the present disclosure is an article of manufacture or "kit," containing materials useful for the treatment or prophylaxis of a tissue or organ transplant rejection or graft-versus-host disease (GVHD) in a subject.

In one embodiment, the kit comprises a container comprising the compound of the present disclosure (i.e., daphnoretin). The kit is suitable for the treatment or prophylaxis of treating a tissue or organ transplant rejection or graft-versus-host disease (GVHD). Suitable containers include, for example, bottles, vials, syringes, blister pack, and etc. The container may be formed from a variety of materials such as glass, or plastic. The container may hold a compound of the present disclosure or a pharmaceutical formulation thereof, in an amount effective for the treatment or prophylaxis of a tissue or organ transplant rejection or graft-versus-host disease (GVHD), and may have a sterile access port, for example, the container may be an intravenous solution bag or a vail having a stopper pierceable by a hypodermic injection needle). The kit may further comprise a label or package insert on or associated with the container. The label or package insert indicates that the composition is used for treating condition of choice. Alternatively or additionally, the kit may further comprise a second container comprising a pharmaceutically acceptable buffer, such as a to phosphate-buffered saline, Ringer's solution or dextrose solution. It may further include other materials desirable from a commercial and user standpoint, including other buffers, diluents, filters, needles, and syringes.

The kit may further include directions for the administration of the compound of the present invention and, if present, the second formulation for treating or preventing a tissue or organ transplant rejection or graft-versus-host disease (GVHD). For example, if the kit comprises a first composition comprising daphnoretin of the present disclosure, and a second pharmaceutical formulation, the kit may further include directions for the simultaneous, sequential, or separate administration of the first and second pharmaceutical compositions to a patient in need thereof.

In another embodiment, the kits are suitable for the delivery of solid oral forms of a compound of the present disclosure, such a kit includes, for example, a number of unit dosages. Such kits include card having the dosages oriented in the order of their intended use. An example of such kit is a "blister pack." Blister packs are well known in the packaging industry and are widely used for packaging pharmaceutical unit dosage forms. If desired, an aid may be provided, for example, in the form of numbers, letters, or other markings or with a calendar insert, designating the days in the treatment schedule in which the dosage can be administered.

According to one embodiment, the Kit may include, at least, (a) a first container containing the daphnoretin; and optionally, (b) a second container containing a second therapeutic agent that is any of a known immunosuppressive agent; and (c) a legend associated with the kit for instructing a user how to use the kit. The legend may be in a form of pamphlet, tape, CD, VCD or DVD.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods

Generation of Human Dendritic Cells (DCs) from Monocytes

Human peripheral blood mononuclear cells were collected from healthy donors and were isolated using Histopaque (Amersham Pharmacia Biotech, Piscataway, N.J., USA) for density gradient centrifugation. Erythrocytes were lysed by using 0.9% ammonium chloride incubated for 3 min at 37° C. Thereafter, $CD14^+$ monocytes were purified by gradient magnetic sorting method using miniMACS system with anti-CD14 microbeads (Miltenyi Biotec, Bergisch Bladbach, Germany). After incubation at 37° C. for 2 hr, nonadherent cells were removed and adherent cells were collected. The purity of isolated $CD14^+$ monocytes was over 90% by using flow cytometric analysis. Immature DCs were generated from $CD14^+$ monocytes by culture in RPMI 1640 medium supplemented with 10% fetal calf serum, 100 ng/mL GM-CSF (Schering-Plough, Munich, Germany), 50 ng/mL IL-4 (R&D Systems, Minneapolis, Minn., USA), and daphnoretin (0, 1.1, 3.3, 10 or 30 µM) every 3 days for 6 days in a humidified 5% $CO_2$ incubator. To trigger maturation of DCs, immature DCs were incubated with lipopolysaccharide (LPS) (5 ng/mL) (Sigma, St. Louis, Mo., USA) and/or a combination of cytokines including 5 ng/mL TNF-α, 5 ng/mL IL-1β, 15 ng/mL IL-6 (R&D Systems, Minneapolis, Minn., USA), and 1 µg/mL prostaglandin E2 (PGE2) (Sigma-Aldrich, St. Louis, Mo., USA) for 24 hr. It has been shown that monocyte-conditioned medium containing a combination of pro-inflammatory cytokines (i.e., TNF-α, IL-1, IL-6, and PGE2) or LPS triggers efficient DCs maturation. Daphnoretin was purchased from Sigma (St. Louis, Mo., USA) and dissolved in PBS as a stock solution (0.5 mg/mL).

Number of Viable Cells

DCs were harvested on day 8 and the number of viable cells was estimated using trypan blue dye exclusion test. The viability of DCs was estimated by dividing the number of harvested DCs by the total number of sorted $CD14^+$ monocytes.

Flow Cytometric Analysis

Dual-color immunostain was performed using fluorescein isothiocyanate (FITC)- and phycoerythrin (PE)-conjugated monoclonal antibodies (mAbs). The mouse anti-human mAbs IgG1:FITC/mouse IgG1:PE, and appropriate isotype controls were purchased from Serotec (Oxford, UK) and used for characterization of DCs. The isotype controls used in our study included anti-CD11c and anti-CD14 (for IgG-FITC), anti-CD1a-PE, anti-CD80-PE, anti-CD83-PE, anti-HLA-DR-PE and anti-DC-SIGN-PE. Cells were incubated with saturating concentrations of PE-conjugated mAbs and primary CD11c mAbs followed by IgG-FITC at 4° C. for 30 min. After washing twice with PBS, $1\times10^6$ cells were applied to a FACS caliber flow cytometer (BD Biosciences, San Jose, Calif., USA). Data were collected and analyzed using CellQuest Software (BD Biosciences, San Jose, Calif., USA).

Morphological Observation

DCs were centrifuged onto microscope slides by means of a Cytospin centrifuge (Shandon Inc., Pittsburgh, Pa.), stained with Wright-Giemsa solution, and observed under light microscopy (Olympus, Tokyo, Japan). Photographs were taken with a digital camera with magnification.

Allogenic Naïve T Cell Proliferation and Cytokine Secretion

Nonadherent cells from culture of isolated mononuclear cells were used to purify naïve T cells. Naïve T cells were enriched with a $CD4^+CD45RA^+T$ cell isolation kit (Miltenyi Biotec) using a MIniMACS system with negative selection technique. Monocyte-derived DCs were harvested and irradiated (3,000 cGy in a single fraction) with 6 MeV X-ray generated by linear accelerator (Clinac® 1800, Varian Associates Inc., CA) at a dose of 4.0 Gy/min. Full electron equilibrium was ensured for each fraction by a parallel plate PR-60C ionization chamber (Capintel Inc., Ramsey, N.J., USA). Thirty Gray-irradiated DCs were incubated with $1\times10^6$ allogeneic naïve T cells at ratios of 1:10 or 1:20 for 5 days, after which, 10 µM 5-bromo-2-deoxyuridine (BrdU) was added to T cell culture for 18 hr. The cells were then collected and the incorporated BrdU was detected using flow cytometry to estimate T cell proliferation.

Immunoblot Analysis

Cells were lysed, and 50 µg of protein extract were electrophoresed in 10% (w/v) SDS-polyacrylamide gels, transferred to nitrocellulose membrane. Membranes were incubated overnight at 4° C. with antibodies against target proteins: anti-phosphorylated p38, anti-phosphorylated extracellular signal-regulated kinase (ERK), anti-phosphorylated c-Jun N-terminal kinase (JNK) (Cell Signaling Technology, Danvers, Mass., USA), or anti-β-actin (at 1:5000 dilution, Sigma, St. Louis, Mo., USA). Membranes were washed and treated with mouse anti-goat IgG (Santa Cruz, Biotechnology) or goat-antirabbit (Santa Cruz, Biotechnology) conjugated to horseradish peroxidase. The antigen-antibody reaction was visualized using an enhanced chemiluminescence assay (Amersham Biosciences) and was exposed to chemiluminesance film (Amersham Pharmacia Biotech, US).

Skin Allograft Transplantation Model

Male C57BL/6($H-2^b$) and BALB/6($H-2^d$) mice aged 6-8 weeks were purchased from Animal Resource Center of National Science Council of Taiwan (Taipei, Taiwan) and maintained in a room with 12 hr light/dark cycles. Standard laboratory chow and water were available ad libitum. All animal experimental procedures were performed in accordance with guidelines and approved by the Animal Care and Use Committee of Mackay Memorial Hospital. The surgery for skin transplantation was performed in accordance with procedures modified from a previous study (Huang et al., Transplantation 2013 95, 791-800). Briefly, a 2×1 cm full-thickness skin graft was harvested from the donor mouse and sutured to the graft bed of a recipient mouse. The skin graft rejection was defined as necrosis of more than 80% of the epidermal surface. Daphnoretin (0.5 or 1.0 mg/Kg) and rapamycin (3.0 mg/Kg) were administered intraperitoneally daily until rejection was observed. Body weight was recorded and the white blood cell count was estimated by an automatic counter.

Statistical Analysis

Results are expressed as the mean±standard error of the mean (SEM), and comparisons were made using Student's t-test. A probability of 0.05 or less was considered significant.

Example 1 Characterization of Daphnoretin 1.1 Daphnoretin Suppresses the Differentiation of DCs In this example, the effects of daphnoretin on the differentiation of DCs were investigated by monitoring its effect on the morphology, cell viability, and expression of differentiation markers on DCs. Results are illustrated in FIGS. 1 to 3.

As the photographs in FIG. 1 depicted, immature DCs had round countours and lacked dendritic formation (FIG. 1, panel A); when they were co-incubated with daphnoretin (1.1, 3.3, 10 or 30 µM), the differentiation process of DCs was suppressed, accordingly, the DCs remained rounded and without the formation of dendrites (FIG. 1, panels B to E).

Figure 2:
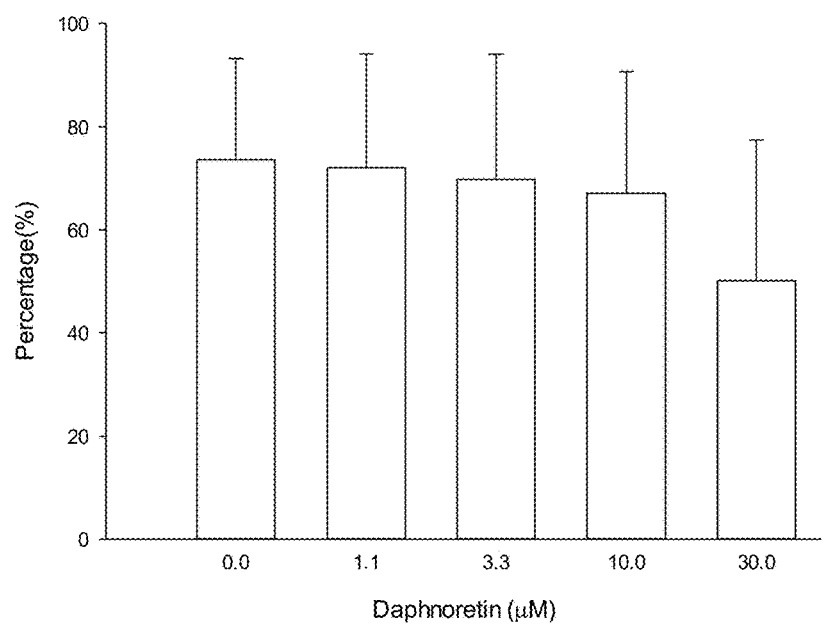
FIG. 2 are bar graphs depicting the effect of daphnoretin on the level of surface marker expressed on monocyte-derived DCs in accordance with one embodiment of the present disclosure, where A. CD1a, B. CD14, C. CD40, D. CD83, E. DC-SIGN.
Figure 2:
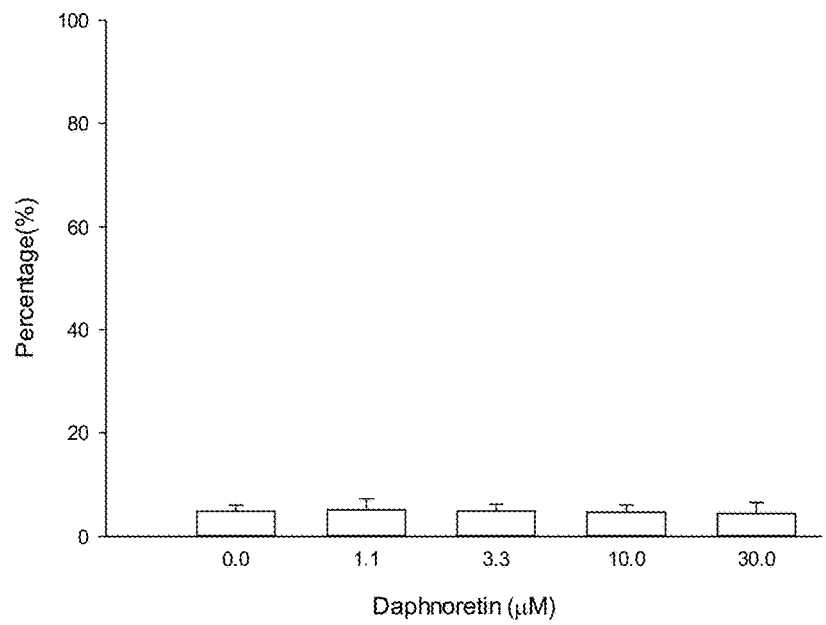
Figure 2:
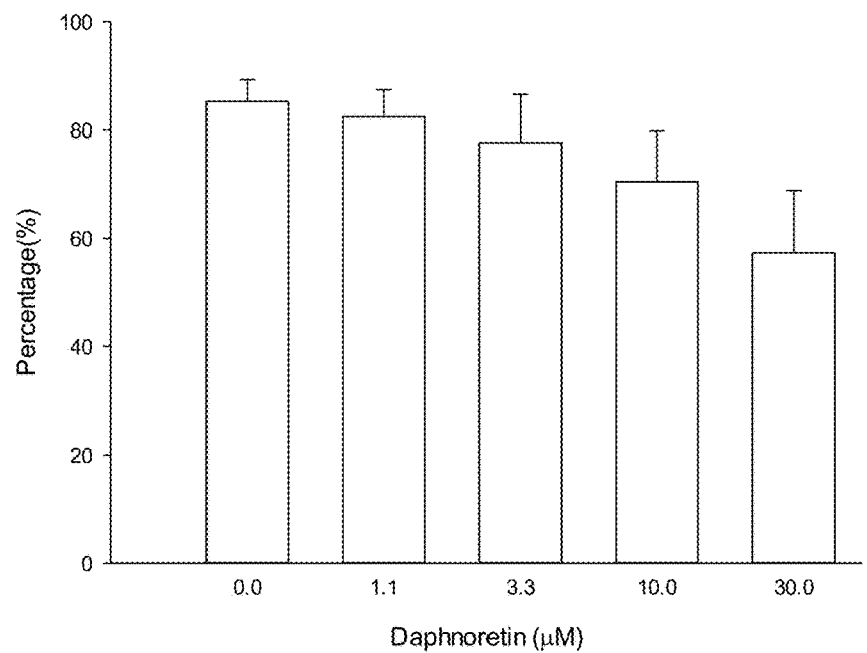
Figure 2:
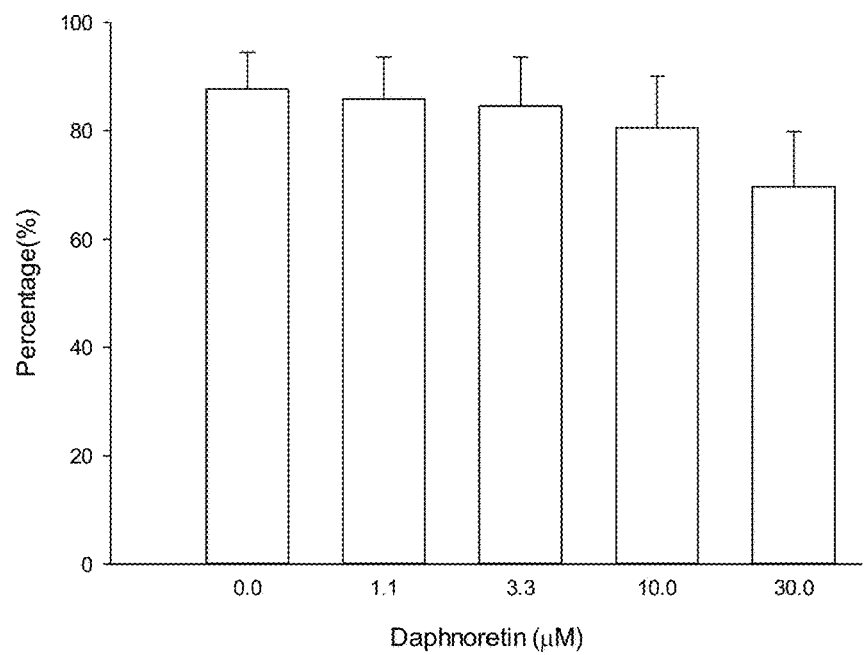
Figure 2:
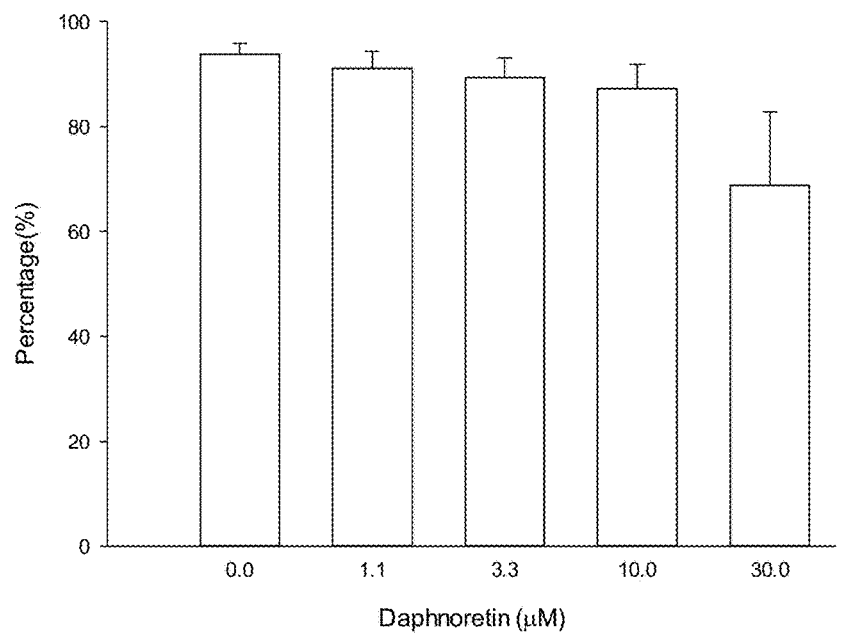
Figure 3:
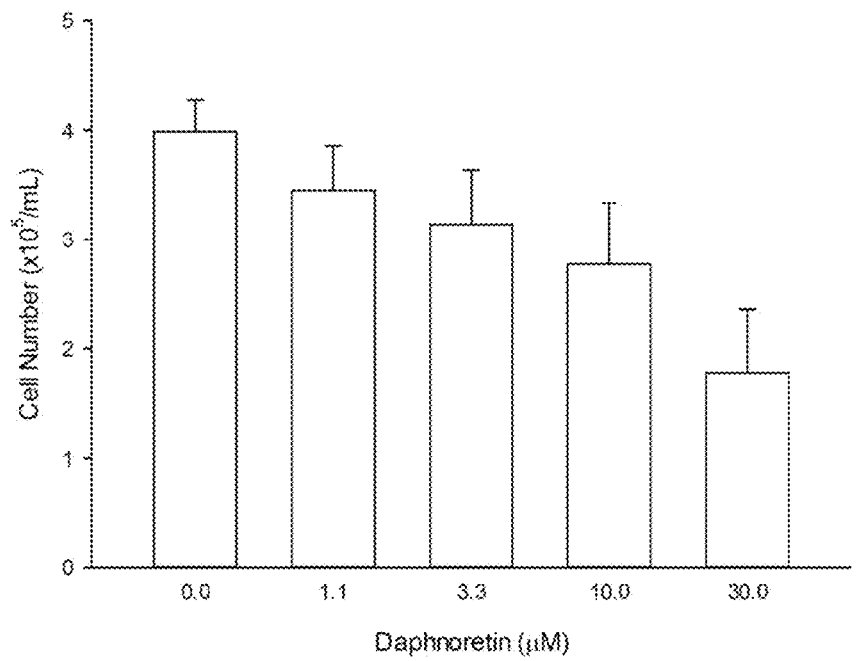
FIG. 3 is a bar graph depicting the effect of daphnoretin on the viability of DCs in accordance with one embodiment of the present disclosure.

The inhibition of differentiation of DCs by daphnoretin also reflected on the expression of cell markers, in which the expression of CD1a, CD40, CD83 and DC-SIGN was suppressed, an indication that the differentiation and maturation toward DCs was inhibited by daphnoretin (FIG. 2, panels A, C, D and E); while the expression of macrophage marker CD14 was unaffected (FIG. 2, panel B).

Further, it was found that daphnoretin affected cell viability. In such cases, daphnoretin (1.1, 3.3, 10 or 30 µM) was added to cell culture medium of DCs, and the viability was determined by trypan blue dye exclusion test. As depicted in FIG. 3, daphnoretin reduced the cell numbers of both mature and immature DCs in dose-dependent manner.

1.2 Daphnoretin Suppresses the Proliferation of $CD4^+CD45RA^+$ Naïve T Cells

Figure 4:
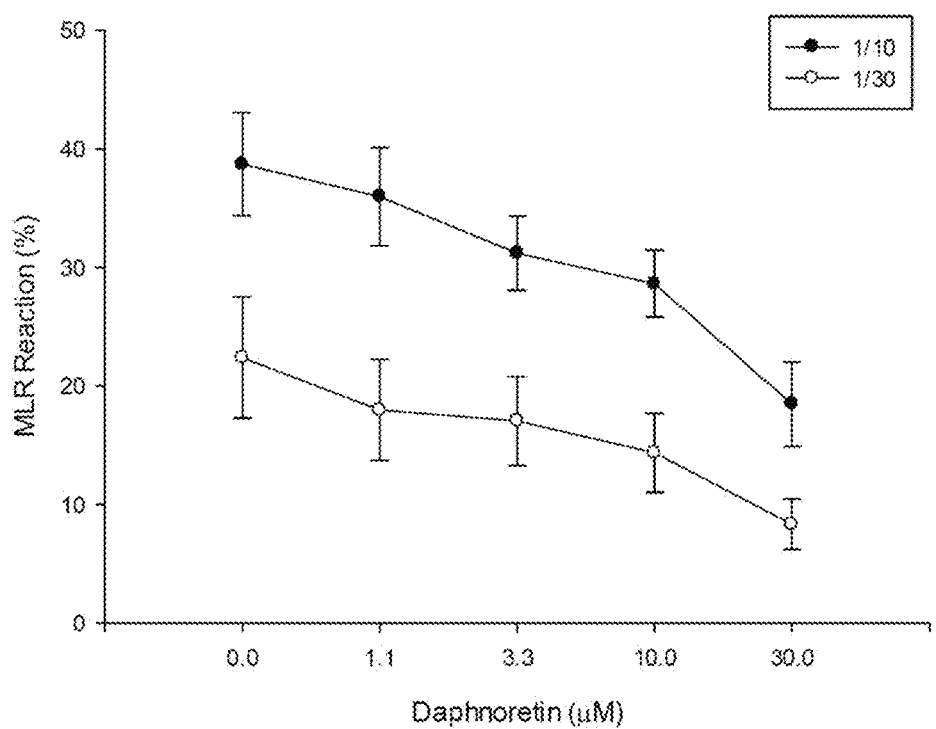
FIG. 4 is a line graph depicting the effect of daphnoretin on the proliferation of $CD4^+CD45RA^+$ naïve T cells stimulated by matured DCs generated in various cultures in accordance with one embodiment of the present disclosure.

In this example, allogenic naïve T cell were isolated and enriched with a $CD4^+CD45RA^+T$ cell isolation kit in accordance with procedures described in the "Materials and methods." Then, mature DCs were co-incubated with the enriched $CD4^+CD45RA^+$ cells at the ratio of 1:10 or 1:30, and the level of proliferation was determined. As the data in FIG. 4 indicated, the proliferation of DCs stimulated T cells was suppressed by daphnoretin, and the suppression level increased with an increase in the concentration of daphnoretin (FIG. 4).

1.3 Daphnoretin Suppressed the Differentiation of DCs Through JNK

Figure 5:
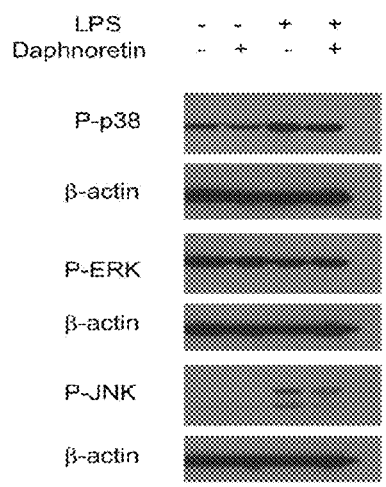
FIG. 5 illustrates the effect of daphnoretin on DC modulation and reversal effect of c-Jun N-terminal kinases (JNK) activator anisomycin in accordance with one embodiment of the present disclosure; A. expression of MAP kinase, B. expression of p-JNK, and C. morphology of DCs, magnification of photograph is 400×.
Figure 5:
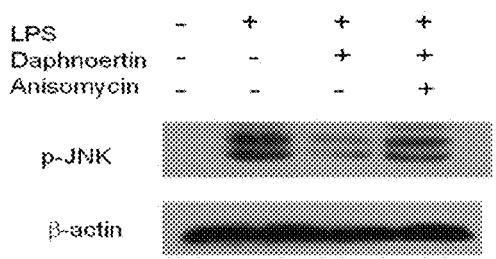
Figure 5:
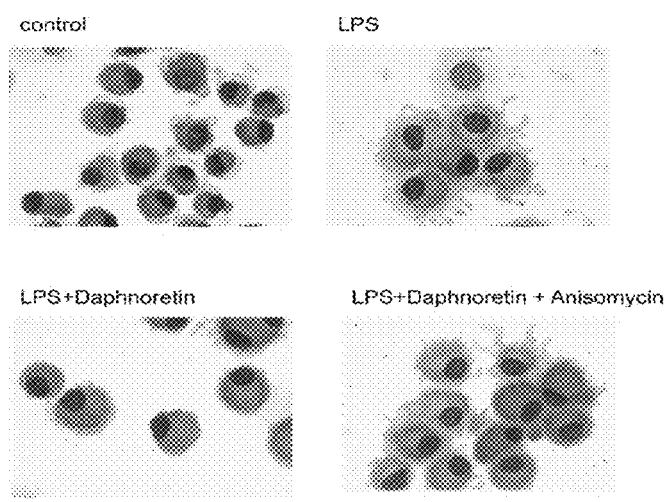

To determine if daphnoretin exerted its function through activation of JNK, $CD14^+$ cells were co-incubated with daphnoretin and anisomycin (i.e., an JNK activator), and the expressed levels of phosphorylated JNK (p-JNK) was measured. It was found that the level of p-JNK decrease in DCs treated with daphnoretin and anisomycin could reverse this decrease (FIG. 5, panels A and B); also, the morphology of DCs treated with daphnoretin and anisomycin remained rounded and without the formation of any dendrites (FIG. 5, panel C).

Example 2 Effects of Daphnoretin on the Survival of Skin Graft

Figure 6:
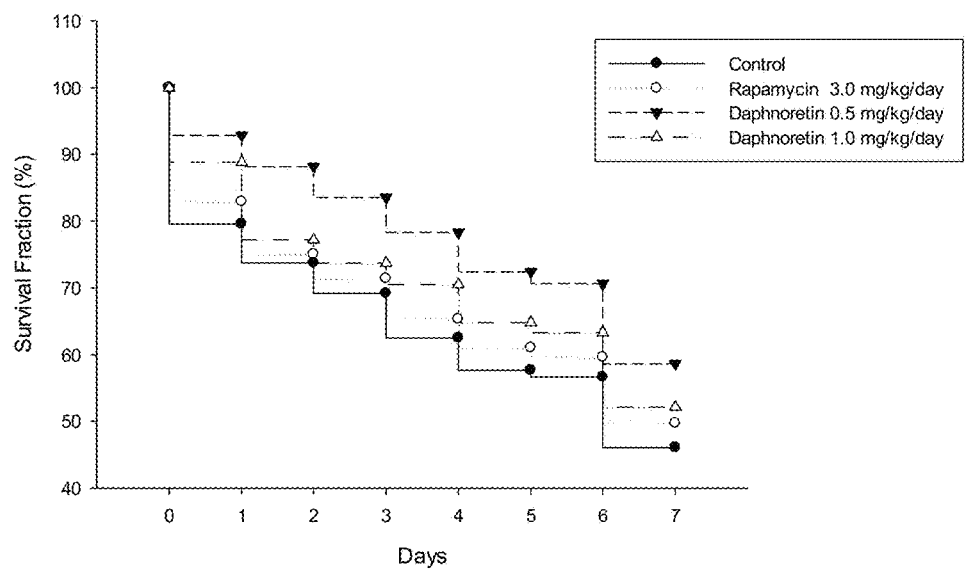
FIG. 6 illustrates the effect of daphnoretin on acute rejection of skin allografts in accordance with one embodiment of the present disclosure; A. survival of skin graft, B. body weight of the recipient mouse, and C. white blood cell count of the recipient mouse.
Figure 6:
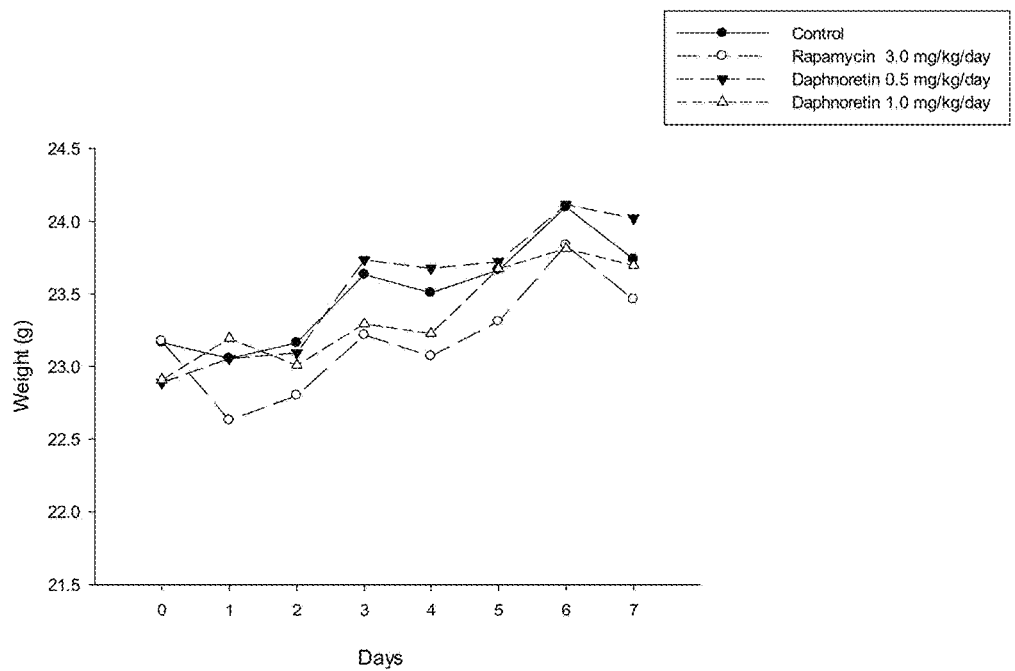
Figure 6:
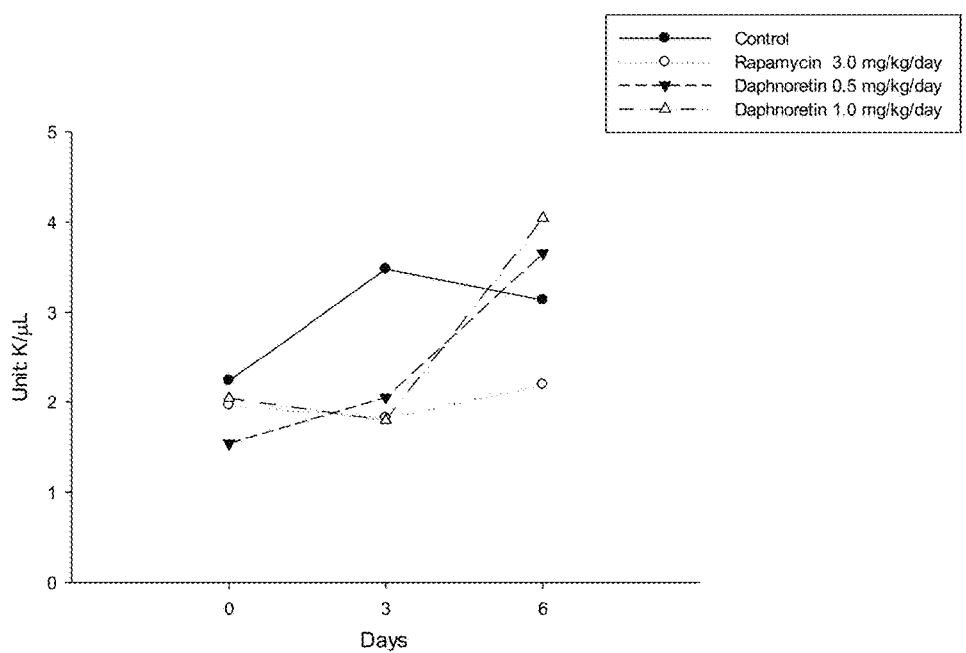

In this example, the effect of daphnoretin on the rejection of a skin graft in a host was investigated. A small piece of skin harvested from a donor mouse was transferred and grafted onto the graft bed of a recipient mouse, whom had received daily treatment of daphnoretin (0.5 mg/Kg/day or 1.0 mg/Kg/day), or rapamycin (a known immunosuppressive agent at the dose of 3 mg/Kg/day) for 7 consecutive days, and the anti-rejection effect was evaluated by the fraction of the skin graft remained viable on the recipient mouse. Results are depicted in FIG. 6.

As expected, rapamycin increased the survival fraction of the skin graft, as compared with that of the control. Surprisingly, in daphnoretin (1.0 mg/Kg/day) treated mouse, the fraction of the survived skin was even higher than that treated of the rapamycin-treated mouse, indicating daphnoretin at the dose of 1.0 mg/Kg/day was effective in suppressing allograft-induced rejection. Further, both the body weight and the white blood-cells-count did not vary significantly at the dose of daphnoretin employed in this example, as compared with that of the control (FIG. 6, panels B and C).

Taken together, the data confirmed that daphnoretin may serve as a candidate compound for the development of anti-allograft rejection medicine.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method for treating a tissue or organ transplant rejection or graft-versus-host disease (GVHD) in a subject in need thereof comprising administering to the subject an effective amount of daphnoretin.

2. The method of claim 1, wherein the daphnoretin is administered in an amount of 0.1-100 mg/Kg.

3. The method of claim 2, wherein the daphnoretin is administered in the amount of 1-50 mg/Kg.

4. The method of claim 3, wherein the daphnoretin is administered to the subject prior to the tissue or organ transplant.

5. The method of claim 1, wherein the tissue is skin, stem cells, or bone marrow.

6. The method of claim 1, wherein the organ is kidney, heart, liver, lung, or pancreas.

7. The method of claim 1, further comprising administering the daphnoretin to the donor tissue or organ prior to transplantation into the subject.

8. The method of claim 1, further comprising administering to the subject an immunosuppressive agent.

9. The method of claim 8, wherein the immunosuppressive agent is selected from the group consisting of cyclosporine, dexamethasone, prednisone, azathioprine, fluorouracil, mercaptopurine, everolimus, sirolimus, tacrolimus, methotrexate, anthracycline, bleomycin, dactinomycin, mithramycin, mitomycin, rapamycin, and mycophenolate mofetil.

10. The method of claim 9, wherein the immunosuppressive agent is rapamycin.

11. The method of claim 1, wherein the subject is a human.

* * * * *